US008657862B2

(12) United States Patent
Irion et al.

(10) Patent No.: US 8,657,862 B2
(45) Date of Patent: Feb. 25, 2014

(54) LIGHT SYSTEM FOR PHOTODYNAMIC DIAGNOSIS AND/OR THERAPY

(75) Inventors: Klaus M. Irion, Liptingen (DE); André Ehrhardt, Wurmlingen (DE); Andreas Schmal, Liptingen (DE)

(73) Assignee: Karl Storz GmbH & Co. KG (DE)

( * ) Notice: Subject to any disclaimer, the term of this patent is extended or adjusted under 35 U.S.C. 154(b) by 1386 days.

(21) Appl. No.: 11/432,014

(22) Filed: May 11, 2006

(65) Prior Publication Data

US 2006/0256544 A1 Nov. 16, 2006

(30) Foreign Application Priority Data

May 11, 2005 (DE) .......................... 10 2005 022 608

(51) Int. Cl.
*A61N 5/06* (2006.01)

(52) U.S. Cl.
USPC .................................. 607/88; 606/11; 606/12

(58) Field of Classification Search
USPC ................. 285/15–52; 606/2–19; 607/88–94
See application file for complete search history.

(56) References Cited

U.S. PATENT DOCUMENTS

| | | | | |
|---|---|---|---|---|
| 4,580,557 A | * | 4/1986 | Hertzmann | 606/12 |
| 4,657,013 A | * | 4/1987 | Hoerenz et al. | 606/4 |
| 4,770,529 A | * | 9/1988 | Levinson et al. | 356/153 |
| 4,775,211 A | * | 10/1988 | Wondrazek et al. | 385/88 |
| 4,860,172 A | * | 8/1989 | Schlager et al. | 362/553 |
| 5,002,051 A | * | 3/1991 | Dew et al. | 607/89 |
| 5,039,191 A | * | 8/1991 | Myszka | 385/31 |
| 5,335,309 A | * | 8/1994 | Fujii et al. | 392/421 |
| 5,396,571 A | * | 3/1995 | Saadatmanesh et al. | 385/33 |
| 5,769,844 A | * | 6/1998 | Ghaffari | 606/16 |
| 5,855,595 A | * | 1/1999 | Fujishima et al. | 607/90 |
| 5,940,554 A | * | 8/1999 | Chang et al. | 385/22 |
| 5,961,543 A | | 10/1999 | Waldmann | |

(Continued)

FOREIGN PATENT DOCUMENTS

| | | |
|---|---|---|
| DE | 34 44 823 C2 | 6/1986 |
| DE | 29517716 U1 | 1/1996 |
| DE | 19539558 A1 | 7/1996 |
| EP | 1 450 190 A1 | 8/2004 |

OTHER PUBLICATIONS

W. Beyer, R. Waidelich, R. Knuechel, H. Stepp, R. Baumgartner, A. Hofstetter: Technical Concepts for White Light Photodynamic Therapy of Bladder cancer. Med. Laser Appl. Chapter 17, pp. 37-40 (2002).
European Search Report, EP06009229, May 26, 2008, 6 pages.

*Primary Examiner* — Bill Thomson
*Assistant Examiner* — Lynsey Crandall
(74) *Attorney, Agent, or Firm* — St. Onge Steward Johnston & Reens LLC

(57) ABSTRACT

A light system for medical photodynamic applications comprises an incoherent light source emitting a light with a power and a light guide which has a distal end and an entrance interface. The entrance interface and the light source have a position relative to one another and are able to be positioned relative to one another. The light system further comprises a luminous power meter for measuring a luminous power emitted at the distal end of the light guide, a motorized positioning unit for positioning the entrance interface and the light source relative to one another, and a control unit which controls the positioning unit as a function of the luminous power measured by the luminous power meter.

31 Claims, 4 Drawing Sheets

(56) References Cited

U.S. PATENT DOCUMENTS

| | | | |
|---|---|---|---|
| 6,214,034 B1 * | 4/2001 | Azar | 607/89 |
| 6,219,584 B1 * | 4/2001 | Lee | 700/90 |
| 6,280,100 B1 * | 8/2001 | Haake | 385/73 |
| 6,413,268 B1 * | 7/2002 | Hartman | 607/94 |
| 6,456,751 B1 * | 9/2002 | Bowers et al. | 385/16 |
| 6,471,692 B1 * | 10/2002 | Eckhouse et al. | 606/15 |
| 6,576,888 B2 * | 6/2003 | Fujimura et al. | 250/227.11 |
| 7,406,227 B2 * | 7/2008 | Anderson | 385/39 |
| 2002/0049432 A1 * | 4/2002 | Mukai | 606/9 |
| 2002/0193849 A1 * | 12/2002 | Fenn et al. | 607/89 |
| 2004/0260365 A1 * | 12/2004 | Groseth et al. | 607/88 |
| 2005/0143793 A1 * | 6/2005 | Korman et al. | 607/94 |

\* cited by examiner

LIGHT SYSTEM FOR PHOTODYNAMIC DIAGNOSIS AND/OR THERAPY

BACKGROUND OF THE INVENTION

The present invention relates to a light system for medical photodynamic applications.

The term "medical photodynamic applications" as used herein refers to photodynamic diagnosis and/or therapy of the human or animal body.

Light systems of this kind are known and are being developed, for example, by the Applicant under the name T-light. Such a light system is described, for example, in W. Beyer, R. Waidelich, R. Knuechel, H. Stepp, R. Baumgartner, A. Hofstetter: Technical concepts for white light photodynamic therapy of bladder cancer. Med. Laser Appl. 17:3740 (2002).

Such light systems are used in photodynamic therapy, for example. In this treatment method, substances called photosensitizers are administered to a patient. These photosensitizers can either be applied specifically to malignant tissue or are more preferably compounds which, by their nature, collect in malignant tissue. When these photosensitizers are irradiated with light of specific wavelengths, a phototoxic effect takes place which can destroy the tissue in which the photosensitizers have collected.

In order to achieve a maximum effect of the treatment, the greatest possible amount of light has to be applied to the tissue treated with the photosensitizer.

In the case of bladder cancer, this is done, for example, using special catheters which comprise a light guide at whose distal end a scattering rod is arranged so that the light introduced into the light guide at the proximal end is distributed across the greatest possible area. To ensure that such light guides can be sterilized and do not lead to a transmission of diseases between patients, they are generally connected to the light source in a detachable manner via a plug.

It has now been found that upon detachment and fitting of the plug into a plug socket of the light system, this plug socket has to be readjusted in order to position the entrance interface of the light guide in the focus of the light source, so as to introduce the greatest possible amount of light into the light guide.

In the previously known systems, this is done by a reference fiber being placed in the plug socket, and the plug socket then being manually adjusted. This reference fiber is then removed from the plug socket and replaced by the proximal end of the light guide. This is an extremely complicated and time-consuming process which considerably reduces the period of time during which such a system is available for patient treatment. Moreover, the adjustment of such a system requires specialized personnel, which considerably increases the costs involved in using this system.

It is therefore an object of the invention to describe a light system in which the adjustment of the position of the entrance interface of the light guide and of the light source relative to one another can be achieved much more easily and quickly, while at the same time ensuring that the greatest possible amount of light is transmitted to the application site.

SUMMARY OF THE INVENTION

In accordance with an aspect of the invention, a light system for medical photodynamic applications is provided, comprising an incoherent light source emitting a light with a power, and a light guide having a distal end and an entrance interface, the entrance interface and the light source having a position relative to one another and being able to be positioned relative to one another, the light system further comprising a luminous power meter for measuring a luminous power emitted at the distal end of the light guide, a motorized positioning unit for positioning the entrance interface and the light source relative to one another, and a control unit controlling the positioning unit as a function of the luminous power measured by the luminous power meter.

Such a system now allows the luminous power at the distal end of the light guide to be directly measured in a simple manner prior to the treatment of a patient. The measured luminous power is then transmitted, together with the position of the entrance interface of the light guide and of the light source relative to one another, to a control unit which then changes the position of the entrance interface of the light guide and of the light source relative to one another such that a desired luminous power is obtained at the distal end of the light guide. This procedure takes place in a fully automated manner and can be completed within a short time, as a result of which the light system can be used much more frequently than a light system that requires manual adjustment. In addition, this adjustment can also be carried out without the involvement of specialized personnel.

Such a light system can therefore be used much more frequently and more cost-effectively.

The expression "distal end of the light guide", as used above and in the remainder of the text, is not limited to the distal interface of the light guide, but also includes light applicators, for example scattering rods, that may be fitted at this interface.

In one embodiment of the invention, the luminous power at the distal end of the light guide can be maximized with the control unit.

Although it is also possible to define other values for the desired luminous power, it is nevertheless more preferable to seek to obtain the highest possible luminous power at the distal end of the light guide. This can be achieved automatically by this measure.

The luminous power is generally maximized by a procedure in which the positioning unit moves in succession the light source and the entrance interface of the light guide relative to one another in three spatial directions within a predefined range and in each case determines the luminous power maximum in the spatial direction. Since the luminous power distribution is a Gaussian distribution, the position of the third maximum represents the total luminous power maximum.

In one embodiment of the abovementioned measure, the luminous power at the distal end of the light guide is maximized by a gradient optimization method.

In a gradient optimization method, the movement of the light source and of the entrance interface of the light guide relative to one another in the three spatial directions is not equidistant, but instead in accordance with the current luminous power gradient. The luminous power maximum is obtained much more quickly in this way.

In a further embodiment of the invention, an IR block filter is provided between the light source and the light guide.

In addition to the white light needed for the photodynamic therapy, incoherent light sources also emit radiation in the IR range (infrared range), i.e. heat radiation. A continuous action of this heat radiation on the proximal end of the light guide can lead to deformations there, and these deformations considerably reduce the efficiency of the introduction of light into the proximal end of the light guide.

From the light that is emitted by the light source, the IR block filter now partially or completely filters out the heat radiation and transmits this to another site, as a result of which the proximal end of the light guide is no longer exposed to heat radiation. In this way, the service life of a light guide can be considerably increased and the efficiency of the introduction of light considerably improved.

In one embodiment of the aforementioned measure, a detector is provided which detects radiation reflected by the IR block filter.

A detector can be used in combination with an IR block filter to measure the intensity of the radiation emitted from the light source, without white light used for the therapy having to be removed from the light.

The luminous power of the light source may decline, for example with age, and this will also lower the power of the infrared radiation. If this is detected by the detector, it is possible, for example, for the output voltage of a power supply of the light source to be increased, in order to drive up the power to the original value.

If this is no longer possible, the information on the luminous power can be used, for example, to prolong the irradiation period as a function of the decline of the luminous power, so as to be able to administer the required radiation dose in each case.

Such a detector can also easily determine whether the light source is still operational.

In a further embodiment of this measure, the power of the light source can be controlled as a function of the radiation detected by the detector.

If a decline in the power of the light source is detected, for example over the course of its service life, this measure means that the power of the light source can be increased automatically, for example via the output voltage of a power supply of the light source, thereby ensuring that the light source always emits light of the same power.

In a further embodiment of the invention, the luminous power at the distal end of the light guide is increased slowly to a maximum value.

It has been shown that, when an irradiation of a patient is carried out, the pain sensation that can occur upon abrupt application of the maximum irradiation is greatly reduced if the power at the distal end of the light guide is increased slowly to the maximum irradiation level.

In a further embodiment of the invention, an operating unit is provided with which the luminous power at the distal end of the light guide can be varied between predeterminable values.

This measure provides remote control, as it were, with which a patient can adjust the luminous power at the distal end of the light guide in order to adapt it to his or her individual sensitivity to pain. If the luminous power is increased, the irradiation time decreases.

In a further embodiment of the invention, the luminous power at the distal end of the light guide is controlled by means of controlling the power of the light source.

This measure, which can be achieved for example by simply changing the output voltage of a power supply of the light source, permits particularly simple control of the luminous power at the distal end of the light guide.

In a further embodiment of the invention, the luminous power at the distal end of the light guide is controlled by means of controlling the position of the entrance interface of the light guide and of the light source relative to one another.

Controlling the power of the light source via the voltage, for example, is possible only within limited ranges, since if the voltage is too low, for instance, the breakthrough fails and no more light is emitted. By means of the abovementioned measure, it is now possible to obtain, at the distal end of the light guide, a luminous power which lies below the power that is possible by only controlling the power of the light source.

In a further embodiment, pulsed light can be emitted by the light source.

Tests have shown that fractionated irradiation, i.e. irradiation with defined interruptions, increases the therapeutic effect of photodynamic therapy. In this case, the frequency of the pulsed light advantageously lies below the response time of pain cells, as a result of which the patient's pain sensation can be further reduced.

In one embodiment of the aforementioned measure, a shutter diaphragm for generating pulsed light is provided on the light source.

By means of this measure, it is possible to operate the light source continuously while the shutter diaphragm opens and closes, resulting in pulsed light being generated. This imposes much less strain on the light source than does rapid switching on and off, for example. In this way, the service life of the light source is greatly increased.

In a further embodiment of the invention, an input unit is provided with which it is possible to define a radiation dose that is to be emitted from the distal end of the light guide, the input unit being able to be used in particular to calculate and adjust an irradiation time as a function of the power of the light source, the position of the entrance interface of the light guide and of the light source relative to one another, and the radiation dose that is to be emitted.

This measure greatly simplifies the operation of a light system, because only a single value has to be entered, and all other values are calculated by the light system itself.

In a further embodiment of the aforementioned measure, the irradiation time is calculated continuously.

During operation of a light system, the power emitted at the distal end of the light guide may suffer changes caused, for example, by a heating of the light source or by the intervention of the patient or an operator. By means of continuous calculation, the irradiation time is automatically adapted to these changes throughout the entire irradiation.

In a further embodiment of the invention, a timer is provided with which the light source can be automatically switched off after the irradiation time has elapsed.

This measure greatly facilitates the work of an operator, since he then only has to apply the light guide to the patient and switch on the light system. There is no longer any need to subsequently check whether the irradiation time has elapsed.

In a further embodiment of the invention, the motorized positioning unit comprises at least one linear motor.

Because of their compact structure and their high degree of precision, linear motors are especially suitable for use in such a positioning unit.

In another embodiment of the invention, a protective cover is provided at the distal end of the light guide, which protective cap can be sterilized and/or is to be disposed of after use.

On account of the electronics present in the luminous power meter, the latter is often not able to be sterilized, or can be sterilized only with difficulty. At the distal end of the light guide, a protective cover can now be provided which ensures that the distal end, which has to be sterile for application to the patient, is not contaminated by the luminous power meter. The protective cover can be sterilizable and therefore reusable, or it can be of the disposable type and simply discarded after use.

It will be appreciated that the features mentioned above and those still to be mentioned below can be used not only in the cited combination, but also in other combinations or singly, without departing from the scope of the present invention.

BRIEF DESCRIPTION OF THE DRAWINGS

Illustrative embodiments of the invention are explained in more detail in the following description and depicted in the drawings, in which.

DETAILED DESCRIPTION OF THE INVENTION

Figure 1:
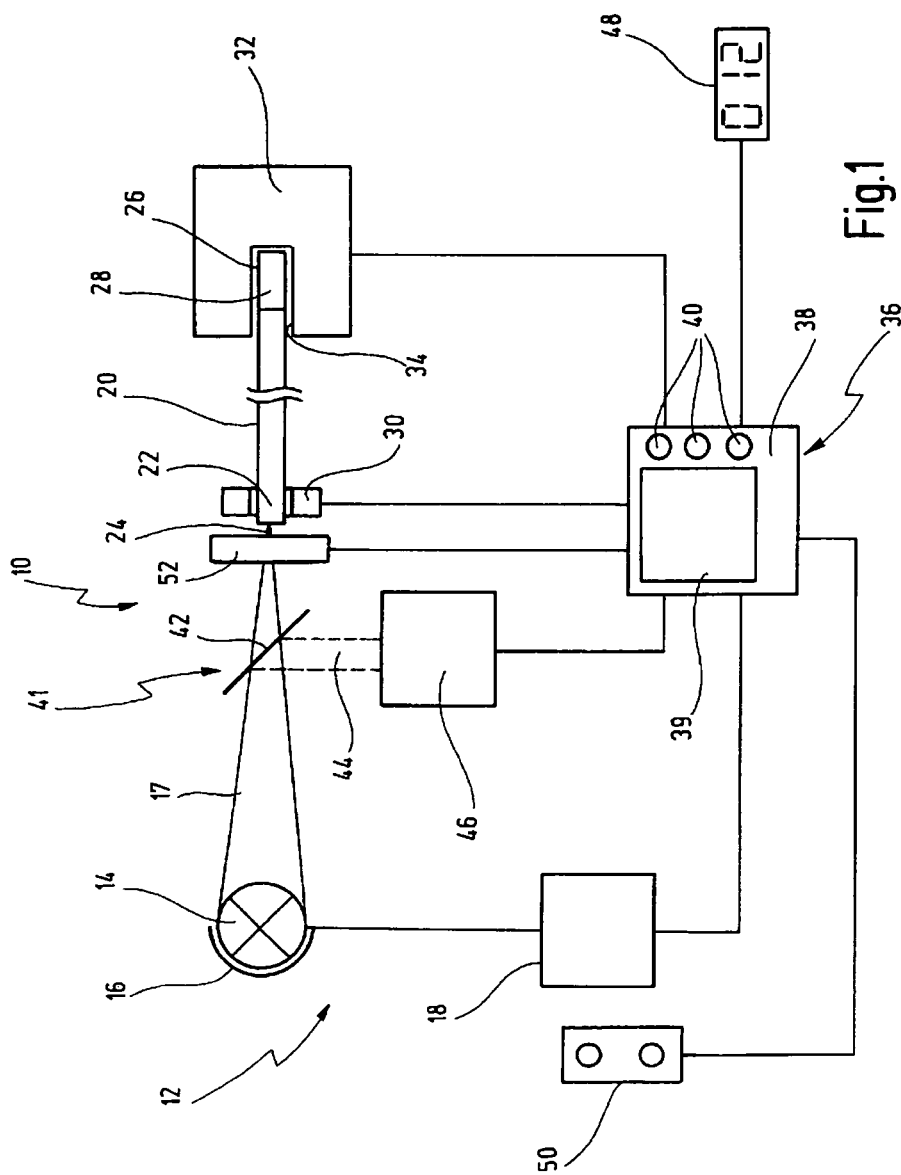
FIG. 1 shows a highly schematic representation of a light system for photodynamic diagnosis and/or therapy.

In FIG. 1, a light system is designated in its entirety by reference number 10.

The light system 10 has a light source 12, which here comprises a xenon short-arc lamp 14, enclosed by a reflector 16 in order to form a directed incoherent light beam 17. The light source 12 also comprises a power supply 18 for the xenon short-arc lamp 14.

The light system 10 further comprises a light guide 20 with a proximal end 22 at which an entrance interface 24 is located, and with a distal end 26 at which a scattering rod 28 is arranged. This scattering rod 28 has the effect that the light introduced into the light guide 20 at the entrance interface 24, and transmitted to the distal end 26, is distributed across the greatest possible area.

The proximal end 22 of the light guide 20 is arranged in a motorized positioning unit 30, while the distal end 26 is inserted into a luminous power meter 32. This luminous power meter 32 has a hollow space 34 into which the distal end 26 of the light guide 20 can be inserted. Arranged in this hollow space 34, there are sensors (not shown here) which measure the luminous power emitted at the distal end 26 of the light guide 20. The luminous power meter 32 and the positioning unit 30 are connected to a control unit 36, here formed by a microcontroller 38.

The luminous power meter 32 now measures the luminous power emitted at the distal end 26 of the light guide 20 and forwards this value to the microcontroller 38. The microcontroller 38 now controls the positioning unit 30 in such a way as to change the position of the proximal end 22 of the light guide 20, and thus of the entrance interface 24, and of the light source 12 relative to one another and in doing so measures continuously the change in the luminous power at the distal end 26 of the light guide 20. When this has reached a maximum in one spatial direction, for example in the x-direction, the movement in this spatial direction is halted and a movement in another spatial direction, for example in the y-direction, is carried out. When the maximum is reached in the third spatial direction, for example in the z-direction, the total maximum of the luminous power at the distal end 26 of the light guide 20 is also reached.

The microcontroller 38 also has a screen 39, here designed as a touch screen, and knobs 40.

The screen 39 can be used for displaying data, such as the momentary luminous power at the distal end 26 of the light guide 20, and also, since it is a touch screen, for selecting special operating modes, such as a slow increase to a maximum value. The knobs 40 also serve for operating the microcontroller 38 and, together with the touch screen, form an input unit.

The light system 10 further comprises an IR block filter 41, which is here designed as a semireflective mirror 42. This semireflective mirror 42 is arranged in the light beam 17 of the light source 12 and reflects an IR component 44 of the light beam 17, here indicated by broken lines, in the direction of a detector 46.

The semireflective mirror 42 is a so-called cold mirror, which permits visible light to pass through and reflects infrared radiation. The visible light passing through the mirror 42 thus causes considerably less heating.

The detector now determines the power of the infrared radiation 44 emitted from the light source 12 and forwards this signal to the microcontroller 38. This signal can also be displayed on the screen 39 and informs an operator of, for example, the state of the xenon short-arc lamp 14. Should the power of the xenon short-arc lamp 14 now decline over the course of time, the microcontroller 38 can control the power supply 18 so as to increase the output voltage for the xenon short-arc lamp 14, as a result of which the power of the xenon short-arc lamp 14 is increased again to its original value. If a further increase of the output voltage is no longer possible, the microcontroller 38 calculates, on the basis of the new luminous power value, a change in the irradiation time and forwards this to a timer 48. When the timer 48 has reached a predetermined value, for example has reached the end of the irradiation time, it forwards a signal to the microcontroller 38, which then switches off the xenon short-arc lamp 14 via the power supply 18.

The light system 10 further comprises an operating unit 50 with which, for example, a patient can vary the luminous power at the distal end 26 of the light guide 20 within predetermined parameters. For example, he can reduce the luminous power if the irradiation is causing an increased pain sensation. He is also able to increase the luminous power, by which means the irradiation time is shortened.

The microcontroller 38 once again registers the changes made by a patient to the luminous power and calculates therefrom continuously a new irradiation time, which is once again forwarded to the timer 48.

The light system 10 further comprises a shutter diaphragm 52 arranged between the light source 12 and the entrance interface 24 of the light guide 20. The light incident on the entrance interface 24 of the light guide 20 can be pulsed by this shutter diaphragm 52, and this leads to enhanced therapeutic efficiency. The shutter diaphragm 52 is likewise connected to the microcontroller 38, and the microcontroller 38 calculates the irradiation time on the basis of the pulse frequency of the shutter diaphragm 52 and forwards it once again to the timer 48. The knobs 40 of the microcontroller 38 can in this case be used, for example, to regulate the pulse frequency of the shutter diaphragm.

Figure 2:
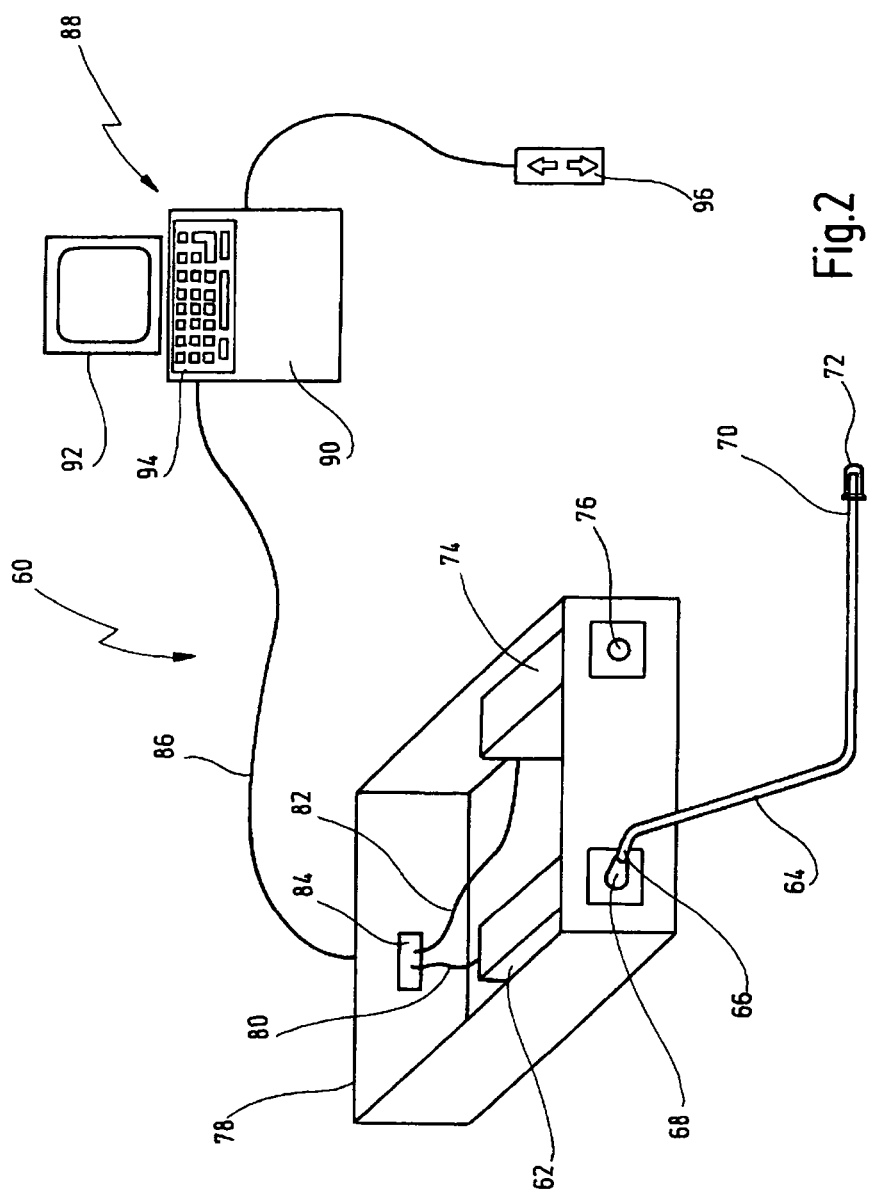
FIG. 2 shows a schematic representation of a further embodiment of a light system for photodynamic diagnosis and/or therapy.

In FIG. 2, a light system is designated in its entirety by reference number 60.

This light system 60 has an illuminating module 62 and a light guide 64. A proximal end 66 of the light guide 64 is arranged detachably in a plug socket 68 of the illuminating module 62. This illuminating module 62 comprises an incoherent light source (not shown here) with which light can be introduced into the light guide 64 arranged in the plug socket 68. Arranged at a distal end 70 of the light guide 64, there is a transparent protective cover 72 which protects the distal end 70 from contamination during the measurement of the luminous power. This protective cover 72 is optically completely transparent in order to avoid distortion of the measurement results. The protective cover 72 is designed to be used just once and is discarded after use.

The light system 60 further comprises a luminous power meter 74 with a socket 76. The distal end 70 of the light guide 64 protected by the protective cover 72 can now be inserted into this socket 76, and the luminous power emitted at the distal end 70 of the light guide 64 can be measured by the luminous power meter. The illuminating module 62 and the luminous power meter 74 are here combined in a housing 78, the upper cover of the housing 78 not being shown here.

A signal line 80 of the illuminating module 62 and a signal line 82 of the luminous power meter 74 are united in a plug 84 on the housing 78 and are connected by means of a cable 86 to a control unit 88.

The control unit 88 is here formed by a personal computer 90 which comprises a screen 92 and an alphanumeric keyboard 94 as input unit. The control unit 88 further comprises an operating unit 96 with which the radiation emitted at the distal end 70 of the light guide 64 can be individually adjusted by a patient.

The treatment of a patient now takes place as follows. The distal end 70 of the light guide 64 is provided with a protective cover 72 and is inserted into the socket 76 of the luminous power meter 74. The luminous power meter 74 measures the luminous power emitted at the distal end 70 of the light guide 64 and transmits this to the control unit 88. The illuminating module 62 transmits to the control unit 88 the relative position of the proximal end 66 of the light guide 64 and of the light source (not shown here) to one another. The control unit 88 now controls the illuminating module 62 and changes the position of the proximal end 66 of the light guide 64 and of the light source relative to one another in one spatial direction. At the same time, the current luminous power gradient of the light emitted at the distal end 70 is measured by the luminous power meter 74. In accordance with this measured luminous power gradient, the control unit 88 changes the distance by which the relative position of the proximal end 66 of the light guide 64 and of the light source to one another is changed, until the maximum is reached in the respective spatial directions.

After completion of this adjustment procedure, the distal end 70 of the light guide 64 is withdrawn from the socket 76 of the luminous power meter 74, and the protective cover 72 is removed from the distal end 70 of the light guide 64.

The distal end 70 of the light guide 64 is now arranged on a patient who is to be treated, and an operator uses the keyboard 94 to enter a maximum irradiation level and a minimum irradiation level and also a desired radiation dose, and then starts the irradiation procedure.

The control unit 88 now slowly increases the luminous power emitted at the distal end 70 of the light guide 64 until the desired maximum value is reached, and it calculates the required irradiation time from the luminous power data and from the desired irradiation dose. During the treatment, a patient is now able to reduce the emitted luminous power via the operating unit 96, for example if the treatment becomes too painful. The control unit 88 registers this change in the luminous power and calculates from this a new irradiation time. At the end of the calculated irradiation time, as determined by a timer integrated in the control unit 88, the light source of the illuminating module 62 is switched off.

Figure 3:
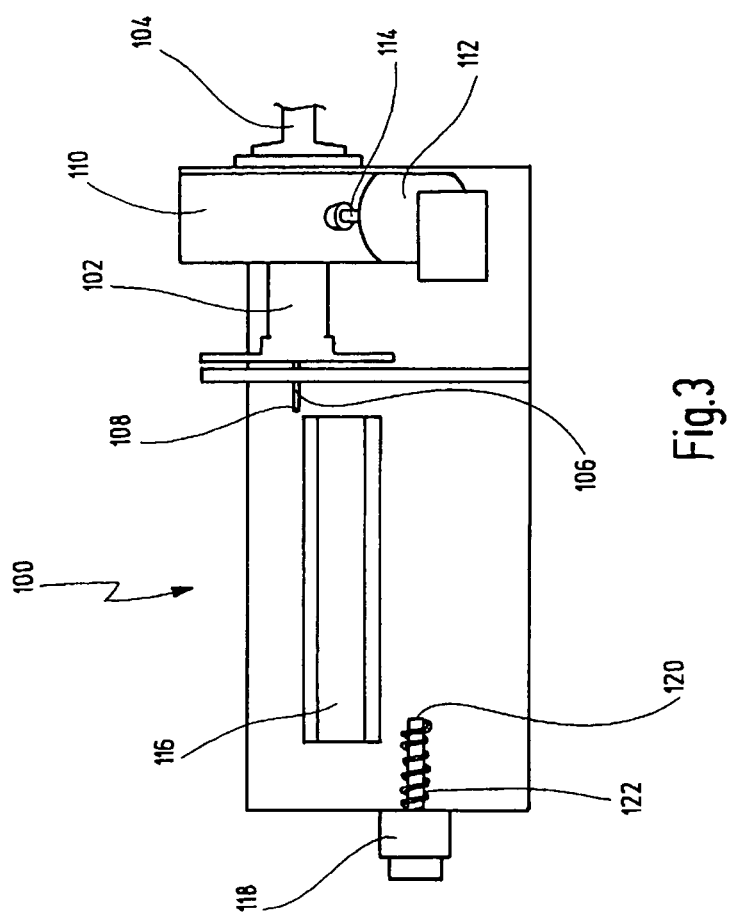
FIG. 3 shows an illumination module of a light system.

In FIG. 3, an illuminating module, as can be used in a light system according to FIG. 2, is designated in its entirety by reference number 100.

To make matters clearer, the light source itself is not shown in this figure.

The illuminating module 100 comprises a plug socket 102 in which a plug 104 of a light guide 106 has been introduced, a proximal end 108 of the light guide 106 protruding from the plug socket 102.

The plug socket 102 is arranged movably in a positioning unit 110. This positioning unit 110 has two linear motors which are arranged at an angle of 90° to one another and of which only a linear motor 112 is visible here. This linear motor 112 has a shaft 114 which can be pushed into the positioning unit 110 or withdrawn from the latter, and thus changes the position of the plug socket 102. The exact structure of this positioning unit 110 is shown in greater detail in FIG. 4.

The illuminating module 100 also comprises a further linear motor 118 which has a shaft 120 with a spring 122.

A light source to be inserted into this illuminating module 100 is arranged to be displaceable along a rail 116, the shaft 120 of the linear motor 118 coming to lie against the light source, and the spring 122 likewise being connected to the light source.

In this illuminating module 100, the positioning unit 110 is now responsible for the movement of the light guide 106 in the x-direction and y-direction relative to the incoherent light source. In this embodiment, the shift in the relative position between the light source and the proximal end 108 of the light guide 106 in the z-direction takes place by displacement of the light source along the rail 116, which is effected by the linear motor 118 and the spring 122.

Figure 4:
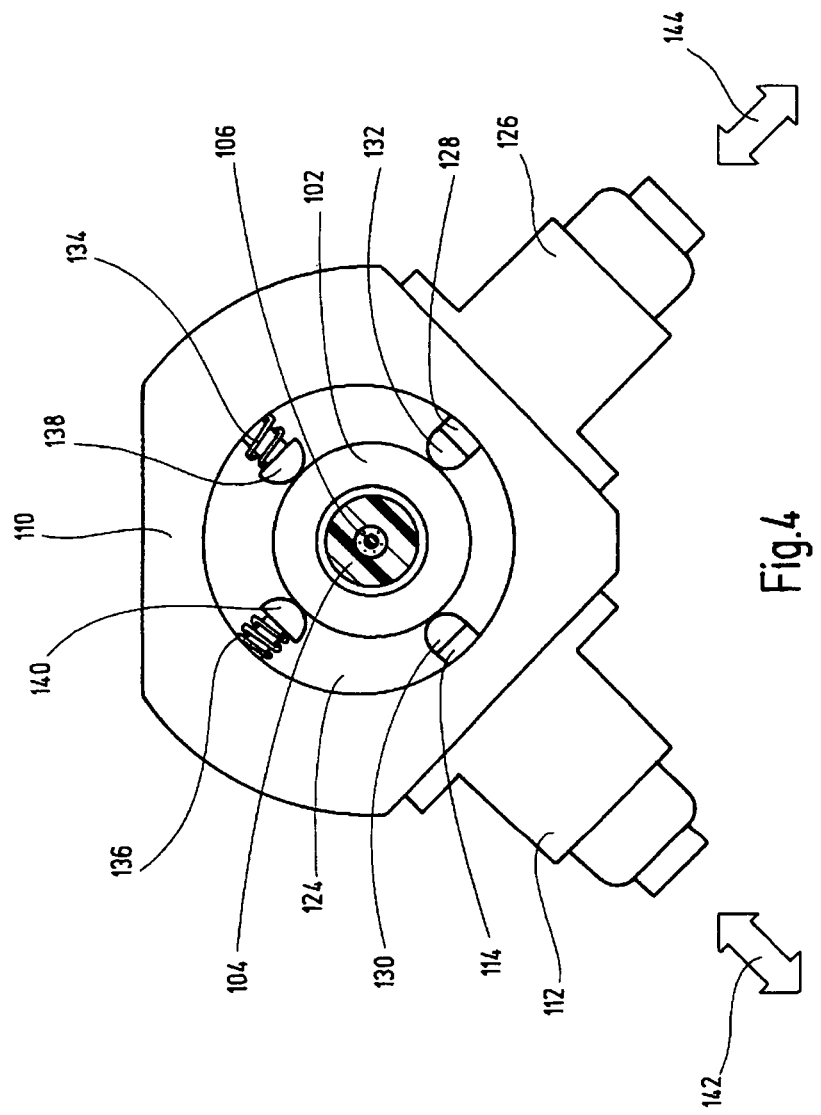
FIG. 4 shows a positioning unit of the illumination module from FIG. 3.

In FIG. 4, the positioning unit 110 of the illuminating module 100 from FIG. 3 is shown in greater detail.

At its center, the positioning unit 110 has a circular opening 124 in which the plug socket 102 is mounted. The plug 104 and the light guide 106 arranged therein are arranged in this plug socket 102.

In addition to the linear motor 112 shown in FIG. 3, the positioning device now comprises a further linear motor 126, which is arranged at an angle of 90° to the linear motor 112. The shaft 114 of the motor 112 and a shaft 128 of the motor 126 extend here into the opening 124 of the positioning unit 110. The two shafts 114 and 128 are likewise arranged at an angle of 90° to one another.

Shaft caps 130 and 132, here designed in the form of hemispheres, are arranged at the outermost end of the shafts 114 and 128. The plug socket 102 comes to lie on the shaft caps 130 and 132. Springs 134 and 136 are arranged opposite the respective motor shafts 114, 128 and shaft caps 130, 132 and have spring caps 138 and 140 arranged at their ends. The springs 134, 136 press the spring caps 138, 140 against the plug socket 102, as a result of which the latter is pressed against the opposite shaft cap 130, 132, respectively.

The linear motors 112, 126 can now move the motor shafts 114, 128 in the direction of the double arrows 142 and 144, respectively. Upon a movement of the motor shafts 114, 128 in the direction of the respective linear motors 112, 126, the springs 134, 136 provide a restoring force, so that the plug socket 102 remains pressed on the shaft caps 132, 130 in each case. By means of the movement of the motor shafts 114, 128 in the direction of the double arrows 142, 144, the plug socket 102 can now be arranged in any desired x/y position in the opening 124 of the positioning unit, as a result of which the positioning of the light guide 106 relative to the light source in two dimensions is obtained.

What is claimed is:
1. A light system for medical photodynamic applications, comprising
 an incoherent light source emitting light with a power,
 a light guide having a distal end and an entrance interface, said entrance interface and said light source having a position relative to one another and being able to be positioned relative to one another,
 a luminous power meter for measuring a luminous power emitted at said distal end of said light guide,
 a motorized positioning unit for positioning said entrance interface and said light source relative to one another, a control unit controlling said positioning unit as a function of said luminous power measured by said luminous power meter, an operating unit for receiving real-time input from a user indicating the user's tolerance to the luminous power and for varying the luminous power based on said real-time input from said user, and an input unit that receives an indication of a total radiation dose that is to be emitted from said distal end of said light guide, said total irradiation dose being a function of both irradiation time and luminous power, said indication of a total irradiation dose being used to continuously calculate and adjust the irradiation time as a function of the power of said light source, and said position of said entrance interface of said light guide and of said light source relative to one another.

2. The light system of claim 1, wherein said luminous power at said distal end of said light guide can be maximized with said control unit.

3. The light system of claim 2, wherein said luminous power at said distal end of said light guide is maximized by a gradient optimization method.

4. The light system of claim 1, wherein an IR block filter is provided between said light source and said light guide.

5. The light system of claim 4, wherein a detector is provided which detects radiation reflected by said IR block filter.

6. The light system of claim 5, wherein said power of said light source can be controlled as a function of said radiation detected by said detector.

7. The light system of claim 1, wherein said luminous power at said distal end of said light guide is ramped up to a maximum value; whereby avoiding the abrupt application of the maximum irradiation level.

8. The light system of claim 1, wherein said luminous power at said distal end of said light guide is variable between predeterminable values, said light system further comprising an operating unit with which said luminous power at said distal end of said light guide can be varied between said predeterminable values.

9. The light system of claim 7, wherein said luminous power at said distal end of said light guide is controllable by controlling said power of said light source.

10. The light system of claim 7, wherein said luminous power at said distal end of said light guide is controllable by controlling said position of said entrance interface of said light guide and of said light source relative to one another.

11. The light system of claim 8, wherein said luminous power at said distal end of said light guide is controllable by controlling said power of said light source.

12. The light system of claim 8, wherein said luminous power at said distal end of said light guide is controllable by controlling said position of said entrance interface of said light guide and of said light source relative to one another.

13. The light system of claim 1, wherein said light is a pulsed light.

14. The light system of claim 13, wherein a shutter diaphragm for generating said pulsed light is provided on said light source.

15. The light system of claim 1, wherein a timer for timing an irradiation time is provided with which said light source can be automatically switched off after said irradiation time has elapsed.

16. The light system of claim 1, wherein said motorized positioning unit comprises at least one linear motor.

17. The light system of claim 1, wherein a protective cover is provided at said distal end of said light guide.

18. The light system of claim 17, wherein said protective cover can be sterilized.

19. The light system of claim 17, wherein said protective cover is to be disposed of after use.

20. A light system for medical photodynamic applications, comprising an incoherent light source emitting light with a power, a light guide having a distal end and an entrance interface near said light source, a luminous power meter for measuring the luminous power emitted at said distal end of said light guide, a control unit controlling the luminous power emitted at said distal end of said light guide, an operating unit for receiving real-time input from a user indicating the user's tolerance to the luminous power and transmitting the real-time input to the control unit to vary the luminous power, and an input unit that receives an indication of a total radiation dose that is to be emitted from said distal end of said light guide, said total irradiation dose being a function of both irradiation time and luminous power, said indication of a total irradiation dose being used to continuously calculate and adjust the irradiation time as a function of the luminous power emitted from said light guide, which is continuously updated in response to change in the real-time input.

21. The light system of claim 20 further comprising a motorized positioning unit for adjusting the luminous power emitted at said distal end of said light guide by positioning said entrance interface and said light source relative to one another.

22. The light system of claim 20 further comprising an adjustable power supply for adjusting the power of said light source and in turn adjusting the luminous power emitted at said distal end of said light guide.

23. The light system of claim 20, wherein said luminous power at said distal end of said light guide is maximized by a gradient optimization method.

24. The light system of claim 20 further comprising an IR block filter between said light source and said light guide.

25. The light system of claim 24 further comprising a detector which detects radiation reflected by said IR block filter.

26. The light system of claim 25, wherein said power of said light source can be controlled as a function of said radiation detected by said detector.

27. The light system of claim 20, wherein said luminous power at said distal end of said light guide is ramped up to a maximum value; whereby avoiding the abrupt application of the maximum irradiation level.

28. The light system of claim 20, wherein said operating unit allows the luminous power at said distal end of said light guide to be variable between predeterminable values.

29. The light system of claim 20, wherein said light is a pulsed light.

30. The light system of claim 20 further comprising a shutter diaphragm on said light source for generating said pulsed light.

31. The light system of claim 20, wherein a timer for timing an irradiation time is provided with which said light source can be automatically switched off after said irradiation time has elapsed.

* * * * *